United States Patent [19]

Cross, Jr.

[11] Plant 4,236

[45] Apr. 4, 1978

[54] PECAN TREE NAMED GRACROSS

[75] Inventor: Harry Cross, Jr., Greenville, Tex.

[73] Assignee: O. S. Gray, Jr., Arlington, Tex.

[21] Appl. No.: 800,180

[22] Filed: May 25, 1977

[51] Int. Cl.[2] ..... A01H 5/03

[52] U.S. Cl. ..... Plt./31

[58] Field of Search ..... Plt./31

*Primary Examiner*—Robert E. Bagwill

*Attorney, Agent, or Firm*—Chas. W. Rummler

[57] ABSTRACT

A new variety of pecan tree distinguished by its vigorous and widely spreading growth habit with longer branches each of which has many smaller and twiggy branches along its length which bear abundant nuts on the interior of the tree mass thereby adding greatly to the total production of nuts which are ordinarily produced mainly at the periphery of the tree mass. This tree is further distinguished by its prolific production of mature nuts which ripen evenly at about midseason and which have a superior cracking quality with a high percentage of nut meats of superior flavor and color.

2 Drawing Figures

BACKGROUND OF THE NEW TREE

This new pecan tree originated as a seedling of unknown parentage at the pecan grove of the late Harry Vernon Cross located along the South Sabine River about 8 miles northeast of the city of Greenville, Tex., and was discovered by me in 1950. The very unusual widely spreading growth of this tree, compared to several hundred seedlings in the same grove, and its prolific production of very fine nuts all along the principal branches of the tree prompted me to asexually propagate the tree in 1952 by grafting propagating wood from the original tree onto a younger tree at my pecan grove at Greenville, Tex., with excellent results, and subsequent propagation of the new tree by both budding and grafting at my Greenville, Tex., pecan grove has demonstrated that all of the distinctive characteristics of the original tree hold true from generation to generation and are firmly fixed in every respect.

DESCRIPTION OF THE DRAWING

My new pecan tree is illustrated by the accompanying drawing which contains a view of a mature tree in its bare state to show its widely spread branching habit, two views of the nut of the new variety, and a view showing a transverse cross-section of the nut.

DESCRIPTION OF THE NEW TREE

GROWTH HABIT

This new pecan tree has a vigorous and widely branching, or spreading, growth habit with longer branches than normally occur in pecan trees and with numerous smaller branches growing along the length of the main branches, these smaller branches bearing clusters of nuts throughout the interior of the tree body or mass which add greatly to the production of nuts which occurs adjacent the ends of the main branches, in the ordinary way of pecan trees. This habit of producing many nuts on the inside branches of the tree in addition to the normal production at the periphery of the tree is a particularly distinguishing characteristic of my new variety of pecan tree.

THE FOLIAGE

The leaves of this new tree are in normal abundance for pecan trees and are of odd-pinnate compound form with 13 to 17 leaflets. Normally the leaflets on vigorously growing shoots are about 4.5 cm. wide and about 13 to 15 cm. long and their color is a dark green.

THE BUDS

The buds of this new pecan tree are typically ovate in shape and are closely spaced on the twigs and branches thereby permitting the formation of numerous fruiting shoots which, in turn, produce numerous clusters of nuts. The buds are borne in clusters on smooth twigs which makes propagation by budding or grafting relatively easy compared to many other pecan varieties.

THE FLOWER

Both staminate and pistillate flowers appear in the early spring, and in the usual manner on the same tree and, since the tree is a protogynous bloomer, its pistillate flowers become receptive before the staminate pollen begins to shed.

THE NUTS

Ripening habit: The nuts ripen evenly and at about mid-season, neither early nor late, and the mature nuts separate easily from the shucks at harvest.

Quantity: The prolific production of nut clusters on both inner and outer branches of the tree, each cluster comprising three or five nuts, results in an extraordinary rate of nut production for trees of this variety, greater than any other pecan variety of the same age and size.

Size and shape: The nuts of this variety are of medium large size, averaging about 4.3 cm. long and 2 cm. across the shoulder and counting from 42 to 44 nuts per pound under good growing conditions. The nut shape is somewhat blocky in form, rather than cylindrical, with a pointed apex and tapering somewhat abruptly at both the basal and apical ends.

Color: The nuts are generally of a light tan color with somewhat broad stripes of a dark purple color extending axially over about $\frac{3}{4}$ of the apical surface and with tiny pinpoint dots of the same color scattered over the basal portion.

Shell and husk: Both the shell and husk of the nuts of this pecan are thinner than of the well known and unpatented Stuart variety, the husk of the mature nut opening readily to release the nut and the thin shell of the nut resulting in a high percentage of quality kernels.

Cracking quality: The thin shell and blocky shape of this new variety of pecan nut permits easy cracking by machine or by hand with a good ratio of whole to half-kernels.

The nut kernels: The kernels are of a light golden brown color and have an excellent flavor. Wide primary grooves extending lengthwise of the dorsal sides of the kernels readily release the "cork" as the nuts are cracked and the kernel halves separate easily from the dividing septum.

Shelling quality: The thin shell of this improved nut results in a very high kernel weight compared with the total weight of the nut. Cracking tests show approximately 59 pounds of kernels resulting from 100 pounds of whole nuts and selected nuts have yielded as high as 62% of kernel.

Disease resistance: My new variety of pecan tree and the nuts produced by it have been entirely free from infection with the pecan "scab" disease, although this tree originated and has been growing among other highly infected varieties, thus indicating a relatively high resistance to that disease.

In general, my new variety of pecan tree is an important addition to pecan tree culture because of the very high production of quality nuts resulting from the widely spreading growth habit of its main branches and the growth of flowering small branches and twigs along the main branches and toward the center of the tree, thus producing nut clusters well inside of the periphery of the tree in addition to the normal nut cluster production occurring adjacent the ends of the main branches. The nuts themselves are highly attractive to the eye both in shape and appearance and their easy cracking quality and high kernel to shell ratio make them a premium product for the marketplace.

I claim:

1. A new variety of pecan tree substantially as herein shown and described, characterized by the spreading habit of growth with numerous twiggy nut clusters producing branches growing along the principal limbs of the tree and well inside the periphery of the tree foliage, and by the prolific production of a medium to large sized thin shell nut having a high kernel to shell ratio and good cracking qualities.

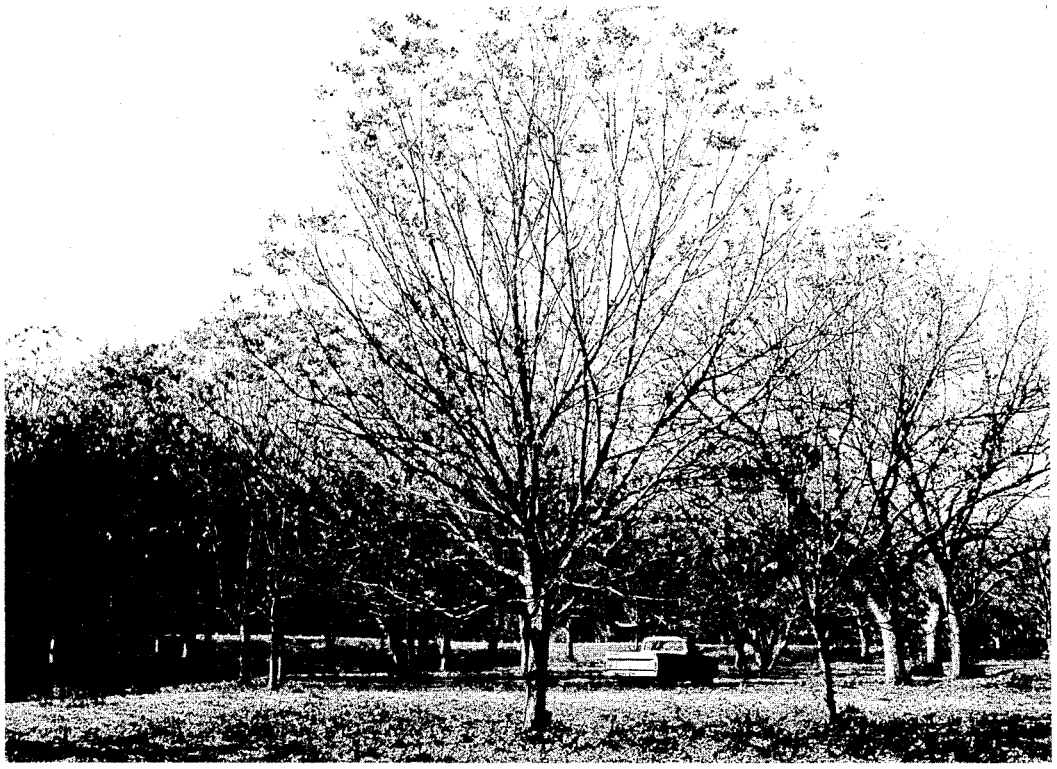
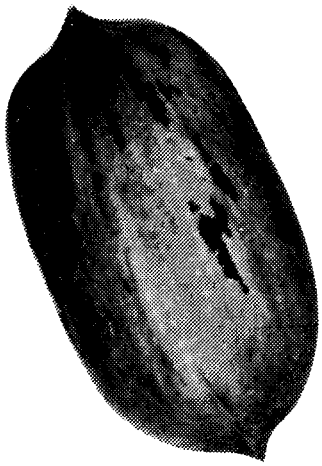
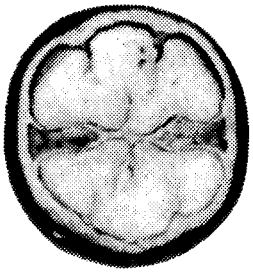
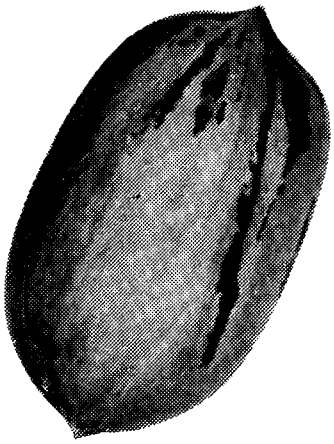

* * * * *